United States Patent [19]

Diamanti

[11] 4,107,316
[45] Aug. 15, 1978

[54] FLUORURATED AMIDES OF NICOTINIC ACID AND THE PROCESS FOR THE PREPARATION THEREOF

[75] Inventor: Enrico Diamanti, Rome, Italy

[73] Assignee: SIGMA-TAU Industrie Farmaceutiche Riunite S.p.A., Italy

[21] Appl. No.: 775,421

[22] Filed: Mar. 8, 1977

Related U.S. Application Data

[63] Continuation-in-part of Ser. No. 610,877, Sep. 5, 1975, abandoned.

[30] Foreign Application Priority Data

Sep. 5, 1974 [IT] Italy ................... 52879 A/74

[51] Int. Cl.² ................... C07D 213/55; A61K 31/44
[52] U.S. Cl. ............................. 424/266; 260/294.8 R; 260/295.5 A
[58] Field of Search ............... 260/295.5 A; 424/266

[56] References Cited

U.S. PATENT DOCUMENTS 3,462,532  8/1969  Hardy ................... 260/295.5 A

Primary Examiner—Alan L. Rotman
Attorney, Agent, or Firm—Robert E. Burns; Emmanuel J. Lobato; Bruce L. Adams

[57] ABSTRACT

A series of physiologically and pharmacologically active novel fluorurated amides of nicotinic acid having the following structural formula:

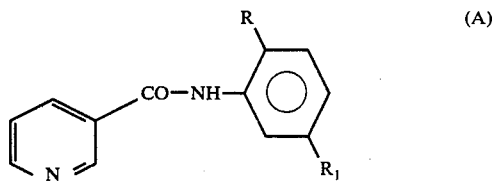

wherein when R is $-NO_2$ or $-NH_2$ then $R_1$ is $-CF_3$ and; when R is $-CF_3$ then $R_1$ is $-NO_2$ or $NH_2$ is described. The products have tranquilizing properties. Compositions for their use are described.

7 Claims, No Drawings

FLUORURATED AMIDES OF NICOTINIC ACID AND THE PROCESS FOR THE PREPARATION THEREOF

This application is a continuation-in-part of now abandoned application, U.S. Ser. No. 610,877 filed Sept. 5, 1975 claiming priority of Italy Pat. No. 52879-A/74 filed Sept. 5, 1974.

THE INVENTION

The object of the present invention is a series of physiologically and pharmacologically active novel fluorurated amides of nicotinic acid having the following structural formula:

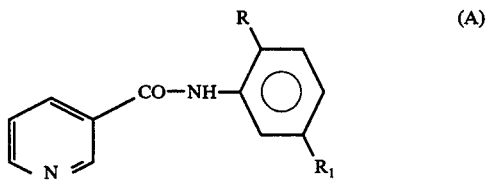

(A)

wherein when R is —$NO_2$ or —$NH_2$ then $R_1$ is —$CF_3$ and; when R is —$CF_3$ then $R_1$ is —$NO_2$ or $NH_2$.

In particular the compounds:

2-nitro-5-trifluoromethyl-anilide of nicotinic acid

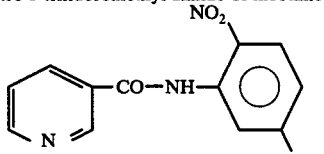

(I)

2-amino-5-trifluoromethyl-anilide of nicotinic acid

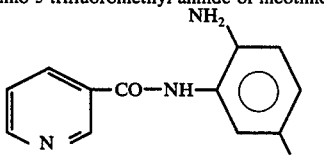

(II)

2-trifluoromethyl-5-nitro-anilide of nicotinic acid

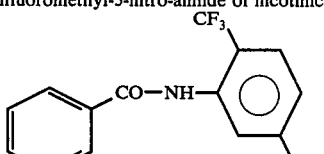

(III)

and
2-trifluoromethyl-5-amino-anilide of nicotinic acid

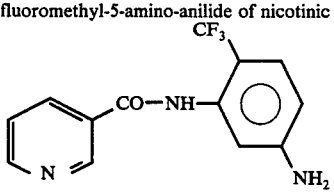

(IV)

are novel.

Compounds (I) and (III) above are intermediates for the preparation of pharmacologically active compounds (II) and (IV).

The present invention includes the process for the preparation of the aforesaid novel compounds and pharmaceutical compositions for the use of the pharmacologically active compounds.

Compounds II and IV also form salts with mineral acids, as for example hydrochloric acid, sulphuric acid, phosphoric acid, etc., or with mono- or pluricarboxylic aliphatic acids, e.g. formic, acetic, lactic, succinic, malonic, glutaric, adipic, tartaric, citric, maleic, fumaric acids, etc., or with aromatic acids, i.e. benzoic, salicylic, pamoic acids, etc., or with mandelic acid, diphenylacetic acid, benzylic acid, etc., or with sulphonic acids, i.e. metansulphonic, benzensulphonic, toluensulphonic, acids, etc., or with sulphamic acids, i.e. cyclamic acid, etc. The pharmaceutically acceptable salts are preferred when the compounds are administered for their pharmacological activity.

Compounds (II) and (IV) showed the following pharmacological activity and properties:

(1) reduction of spontaneous motor activity,
(2) motor decoordination,
(3) deconditioning effect,
(4) anticonvulsive effect, Max E. S and Cardiazol,
(5) amphetamine antagonizing effect,
(6) capability to increase barbiturate-induced hypnosis,
(7) hypothermal activity,
(8) analgesic activity,
(9) High therapeutic index.

In view of the low toxicity properties of compounds II and IV, they are useful as psychotropic drugs i.e. as tranquilizers and for the control of CNS excitement. The pharmacological properties are characteristic for these fluorated amides of nicotinic acid and differ generally from the properties of nicotinic acid per se. The compounds do not cause the characteristic peripheral vasodilation of nicotinic acid.

Further compounds II and IV do not cause toxic side effects after single daily consecutive repeated administration (40 days) of 150 mgm/Kg (per os) in rats.

Both compounds form a new class of psychotropic drugs and are useful in daily doses of between 25 – 300 mgm in control of CNS excitement states.

PHARMACOLOGICAL ACTIVITY AND TOXICITY

$LD_{50}$

Compound II has an $LD_{50}$ of 1200 mg $kg^{-1}$ per os in mice and 850 mg $kg^{-1}$ per os in rats;

Compound IV has an $LD_{50}$ 1200 mg $kg^{-1}$ per os in mice and 800 mg $kg^{-1}$ per os in rats.

$LD_{50}$ and $ED_{50}$ were calculated in accordance with:

J. T. Lichfield and Wilcoxon F., "A Simplified method of evaluating dose-effect experiments", *J. Pharm. Exep. Therap.* 94, 99–113 (1949).

(1) Reduction of spontaneous motor activity:

200 mg $kg^{-1}$ per os reduced by 50% the spontaneous motor activity in rats. Movements were recorded by Animex apparatus (Farad-Coopenaghen).

The reduction of spontaneous motor activity was studied in accordance with the procedure of:

Dews, P., "The measurement of the influence of drugs on voluntary activity in mice", *Brit. J. Pharmacol.* 8, 46, (1959) and Kuhn, W. L. et al., *J. Pharmacol, Exeptl. Therap.* 134, 60 (1961).

The $ED_{50}$ of compounds II and IV were approximately 200 mgm/KG.

(2) Motor Decoordination:

200 mg kg$^{-1}$ per os reduced the Rotarod performance (16 r.p.m.) in rats by the method of Janssen, P. A. et al. "Effect of various drugs on isolation-induced fighting behaviour of male mice", *J. Pharmacol. Exptl. Therap.* 129, 471, (1960).

The ED$_{50}$ for compounds II and IV were substantially 200 mgm/Kg.

(3) Deconditioning effect:

Compounds II and IV exhibited intense deconditioning activity in rats pretrained in seven previous consecutive sessions—50 trials per session—which had acquired an avoidance response in a Shuttle box (80% of avoidances); Deconditioning ED$_{50}$ at 60 min after treatment was 150 mg kg$^{-1}$ os (Litchfield and Wilcoxon).

End-point: No. of rats per group which reduced avoidances by 50% versus the previous trials.

The deconditioning effect was studied in accordance with:

Bovet A., et al., "A programming and recording method for establishing learning, retention and deconditioning curves", *Sci. Rept. Ist. Sup. San.*, 1, 127, (1961).

The ED$_{50}$ for compounds II and IV were substantially 150 mgm/KG.

(4) Anticonvulsive effect:

Compound II at the dose level of 260 mg kg$^{-1}$ and compounds IV at the dose level of 65 mg kg$^{-1}$ brought about death at 60 min after 100 mg kg$^{-1}$ of pentylentetrazole was given to rats.

Against convulsions produced by electric shock the compounds exhibited a powerful protective effect ED$_{50}$ in rats was respectively 32 mg kg$^{-1}$ os for Compound II and 100 mg kg$^{-1}$ os for compound IV (Litchfield and Wilcoxon).

End-point: no. of rats in each group which reduced the hind leg tonic extensor component.

The Anticonvulsive effect was studied in accordance with:

Barnes, J. H. et al., *J. Pharm. Pharmacol.* 13, 39 (1961).
Kerley, Richards D. G. et al., *J. Pharmacol. Exeptl. Therap.* 132, 360, (1961).
Holland G. F. et al., *J. Med. Pharm. Chem.* 3, 1, 99, (1961), and
E. A. W. C. Brown et al., "Comparative assays of antiepileptic drugs in mice and rats" *J. Pharmacol. Exper. Therap.* 106, 319 (1952).

(5) Amphetamine-antagonising effect:

260 mg kg$^{-1}$ os of compounds II and IV reduced by 50% the amphetamine-induced toxicity in grouped mice. i.e. ED$_{50}$ = 260 mg/Kg.

200 mg kg$^{-1}$ os of both compounds reduced the hypermotility which is induced in mice after administering 1-mg kg$^{-1}$ i.p. of amphetamine. ED$_{50}$ = substantially 200 mg/Kg.

The amphetamine antagonizing effect was studied in accordance with:

Piala J. J. et al., *J. Pharmacol. Expetl. Therap.* 127, 55, 1959.
Gardocky J. F. et al., Reconsideration of the central nervous system pharmacology of amphetamine— Toxicity in grouped and isolated mice— *Toxicol. Appl. Pharmacol.* 8, 550–557 (1965).
Gardocky J. K. et al., Reconsideration of the central nervous system pharmacology of amphetamine—Influence of pharmacologic agents on cumulative and total lethality in grouped and isolated mice. *Toxicol. Appl. Pharmacol.* 9, 536–554 (1966).

(6) Capability to increase barbiturate-induced hypnosis:

The duration of the absence of the righting reflex due to barbiturate (Evipan 75 mg kg$^{-1}$ e.p.) in mice was increased (+ 50%) 1 hour after administering 13 mg kg$^{-1}$ os of compound II and 45 mg kg$^{-1}$ of compound IV respectively in accordance with:

Kuhn W. L. et al., *J. Pharmacol. Exptl. Therap.* 134, 60 (1961).

The ED$_{50}$ for compound II was substantially 13 mg/Kg and 45 mgm/Kg for compound IV.

(7) Hypothermal activity:

Both compounds II and IV, induced hypothermia 60 min after 130 mg kg$^{-1}$ os was administered in rats.

Body-temperature decreases: At max — 1° C. by the method described in "Screening Methods In Pharmacology" by R. A. Turner, Academic Press—New York and London 1965 page 92.

(8) Analgesic activity:

Compounds II and IV are exhibited in a marked analgesic action.

Against intraarticular pain due to AgNO$_3$ administration in rats: both compounds at the dose level of 130 mg kg$^{-1}$ os reduced by 50% the response versus the previous trial. (ED$_{50}$ = 130 mgm/Kg).

Against phenylquinone writhing test in mice: both compounds at the dose level of 130 mg kg$^{-1}$ reduced by 50% the no. of spasms versus control group. (ED$_{50}$ = 130 mgm/Kg).

Against the hot-plate test in mice: Compound II at the dose level of 130 mg kg$^{-1}$ os, (ED$_{50}$ = 130 mg/KG) and compound IV at the dose level of 100 mg kg$^{-1}$ (ED$_{50}$ = 100 mg/Kg) increased by 50% the reaction time (liking) versus the previous trial.

Analgesic testing in accordance with:

La Belle and Tislow, *J. Pharmacol.*, 98, 19 (1950).
Hendeesrhot L. C. and Forsaith J., *J. Pharmacol. Exeptl. Therap.* 125, 237 (1959), and
Janssen P. A. J., Jageneau A., *J. Pharm. Pharmacol.* 9, 381 (1957).

PREPARATION

The method of preparation of these compounds comprises reacting an activated form of nicotinic acid such as the chloride or methylester, with either appropriate aniline; 2-nitro-5-trifluoromethyl-aniline and 2-trifluoromethyl-5-nitroaniline.

From the above reaction, compounds (I) and (III), which are novel intermediates, are reduced by a reducing agent such as hydrogen, using Ni/Raney as the catalyst, to form compounds (II) and (IV).

Sequence (a)

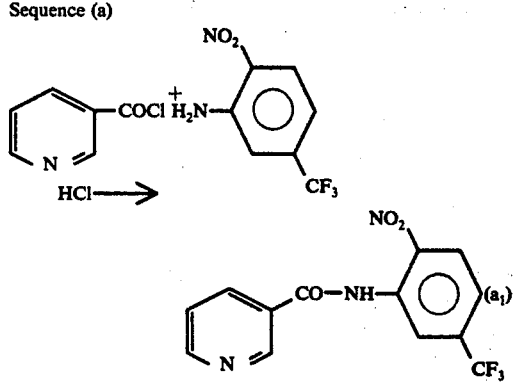

Sequence (a₂)(I)

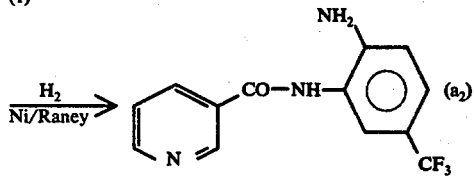

Sequence (b₁)

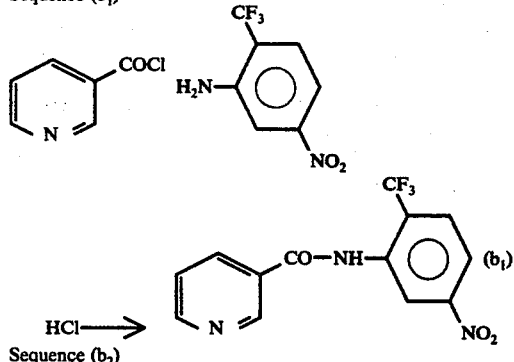

Sequence (b₂)(III)

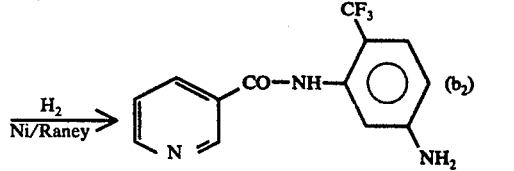

In both sequences (a₁) and (b₁) the reaction is effected by adding 2-nitro-5-trifluoromethyl-aniline or 2-trifluoromethyl-5-nitro-aniline to nicotinoyl chloride or to methylester of nicotinic acid in an inert solvent such as THF, or dioxan; compounds (I) and (III) are obtained.

When nicotinoylchloride is used it is advisable to employ an acceptor of the hydrochloric acid which is formed, as at least a portion of the solvent may include, trimethylamine, triethylamine, pyridine, morpholine, etc., for such a purpose.

The reduction of compounds (I) and (III) is carried out with hydrogen at normal pressure or under pressure using Ni/Raney as the catalyst; it is preferable to use ethanol as the reduction solvent. Non-restrictive examples of the preparation of compounds I, II, III and IV are given below.

EXAMPLE 1 (a₁)

Add 10 g of nicotinic acid to 20 ml of thionyl chloride. Reflux for about 20 hours; then distill and discard the excess of thionyl chloride at reduced pressure. Dissolve the residue with benzene and bring to dryness. Add 30 ml of anhydrous tetrahydrofuran, 6 ml of triethylamine and 10 g of 2-nitro-5-trifluoromethyl-aniline to the dried residue. Reflux for 15 hours, filter the precipitate and while still moist pour the precipitate into a saturated sodium bicarbonate solution. Filter the precipitate and dry at 40° C in vacuo. 10 g of 2-nitro-5-trifluoromethylanilide of nicotinic acid (I), m.p. 135°-6° C (ethanol), is obtained.

EXAMPLE 2 (a₂)

Suspend 10 g of 2-nitro-5-trifluoromethyl-anilide of nicotinic acid in 65 ml of absolute ethanol; add 1.5 ml of Ni/Raney, activated and washed with absolute ethanol, to the suspension. Leave under vigorous stirring in a hydrogen catalytic reducing apparatus at normal pressure, until 2.8 liters of hydrogen has been absorbed. When this operation has been completed, remove the Ni/Raney by filtration and saturate the filtered solution with gaseous hydrochloric acid. Filter the resulting solid and wash with ethyl ether. Dry at 40° C in vacuo. About 15 g of 2-aminotrifluoromethyl-anilide of nicotinic acid (II) is thus obtained in the form of the dihydrochloride which after isopropanolmethanol (9:1) recrystallization has a melting-point of 250°-2° C.

EXAMPLE 3 (b₁)

Add 20 ml of thionyl chloride to 10 g of nicotinic acid. Reflux for about 20 hours; then distill and discard the excess of thionyl chloride at reduced pressure. Dissolve the residue with benzene and bring to dryness. Add 30 ml of anhydrous tetrahydrofuran, 6 ml of triethylamine and 10 g of 2-trifluoromethyl-5-nitro-aniline to the residue. Reflux for 40 hours; filter the precipitate and while still moist slowly pour it into a saturated sodium bicarbonate solution. Filter the resulting solid and dry at 40° C in vacuo. 10 g of 2-trifluoromethyl-5-nitro-anilide of nicotinic acid (III) m.p. 173°-5° C (ethanol) is obtained.

EXAMPLE 4 (b₂)

Suspend 10 g of 2-trifluoromethyl-5-nitro-anilide of nicotinic acid (III) in 60 ml of absolute ethanol.

Add 0.3 ml of Ni/Raney activated and washed with absolute ethanol to the resulting suspension. Leave under vigorous stirring, in a catalytic hydrogen reducing apparatus at normal pressure, until 2.8 liters of hydrogen has been adsorbed. When this operation has been completed, eliminate the Ni/Raney content by filtration and saturate the filtered solution with gaseous hydrochloric acid. Filter the resulting solid and wash with ethyl ether. Dry at 40° C in vacuo. About 8 g of 2-trifluoromethyl-5-aminoanilide or nicotinic acid (IV) is thus obtained in the form of dihydrochloride which after isopropanol-methanol (9 : 1) recrystallization has a melting-point of 230°-2° C.

EXAMPLE 5 (a₁ or b₁)

Add 20 ml of dioxan and 10 g of 2-trifluoromethyl-5-nitroaniline or 2-nitro-5-trifluoromethyl-aniline to 12 g of nicotinic acid methyl ester. Reflux for 60 hours; then pour the reaction mass into water. Filter the resulting solid and recrystallize several times from ethanol. 5 g of (I) or (III) are thus obtained with the same melting-point values as the products of Examples 1 and 3.

The pharmaceutical compositions of this invention comprise the pharmacological active ingredients i.e. compounds II and IV, in pharmacologically effective amounts, incorporated into pharmaceutically acceptable carriers or diluents. The compositions may take any of the forms customarily employed for the administration of therapeutically active substances, but the preferred types include; solutions, syrups and emulsions, pills and capsules, tablets, including sustained release formulations for oral administration. For parental administration, solutions and suspensions may be utilized. The tablets and pills may be formulated in the usual manner with one or more pharmaceutically acceptable diluents or excipients, and can include lubricants useful in the tablet-making art. Capsules made of absorbable material such as gelatin, may contain the active substance alone or in a mixture, with a solid or liquid diluent. Liquid preparations may be in the form of suspension, emulsions, syrups or elixirs of the active substance in water or with other suitable media commonly used for making orally-acceptable pharmaceutical preparations. For external use, it is preferred to dissolve or suspend the active ingredient in an emolient liquid such as purified corn oil or to emulsify it therein and then to incorporate this liquid into a suitable ointment base such as into petrolatum. By first diluting the active ingredient into the emolient liquid, adequate distribution of the active material is assured throughout the ointment base.

The pharmacological and physiological effects for which compounds II and IV are used as tranquilizers and as CNS depressants in treating syndromes characterized by excess CNS stimulation.

What is claimed:

1. A compound of the structural formula:

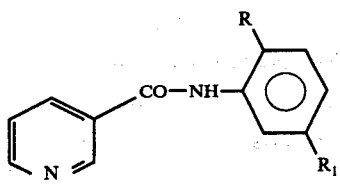

when R is —NO$_2$ or NH$_2$, R$_1$ is —CF$_3$ and;
when R is —CF$_3$, R$_1$ is —NO$_2$ or NH$_2$; and their salts with pharmacologically acceptable acids.

2. The compound according to claim 1:
2-nitro-5-trifluoromethyl-anilide of nicotinic acid.

3. The compound according to claim 1:
2-amino-5-trifluoromethyl-anilide of nicotinic acid and its pharmacologically acceptable salts.

4. The compound according to claim 1:
2-trifluoromethyl-5-nitroanilide of nicotinic acid.

5. The compound according to claim 1:
2-trifluoromethyl-5-aminoanilide of nicotinic acid and its pharmacologically acceptable salts.

6. A pharmaceutical composition comprising a compound according to claim 1 in an effective amount in unit dosage form in combination with a pharmaceutically acceptable vehicle.

7. The method of treating mammals in excited states which comprises administering to said mammals an effective amount in unit dosage form of a composition according to claim 6.

* * * * *